United States Patent [19]

Habib et al.

[11] Patent Number: 4,910,224

[45] Date of Patent: Mar. 20, 1990

[54] METHOD OF MODIFYING THE LIPID STRUCTURE AND FUNCTION OF CELL MEMBRANES AND PHARMACEUTICAL COMPOSITIONS FOR USE THEREIN

[76] Inventors: Nagy A. Habib, 15 The Cedars, St. Stephens Rd., Ealing, London W13, England; Christopher B. Wood, 'Rosemary', Market Place, Chalfont St. Peter, Buckinghamshire SL9 9DS, England; Kosta Apostolov, 15 Canterbury Close, Beckenham, Kent BR3 2EP, England; William R. Barker, 3 Braintree Road, South Ruislip, Middlesex, England

[21] Appl. No.: 14,570

[22] Filed: Feb. 13, 1987

[30] Foreign Application Priority Data

Feb. 14, 1986 [GB] United Kingdom ............... 8603621

[51] Int. Cl.⁴ .............................................. A61K 31/20
[52] U.S. Cl. ..................................... 514/558; 514/572
[58] Field of Search ............................. 514/558, 572

[56] References Cited

U.S. PATENT DOCUMENTS

| | | | |
|---|---|---|---|
| 3,741,204 | 6/1973 | Thiele | 128/92 R |
| 3,805,776 | 4/1974 | Thiele | 128/92 G |
| 3,856,976 | 12/1974 | Hunter et al. | 514/572 |
| 3,993,775 | 11/1976 | Williams | 424/312 |
| 4,097,602 | 6/1978 | Silver et al. | 424/305 |
| 4,273,763 | 6/1981 | Horrobin | 424/145 |
| 4,302,447 | 11/1981 | Horrobin | 424/145 |
| 4,386,072 | 5/1983 | Horrobin | 424/127 |
| 4,388,324 | 6/1983 | Horrobin | 424/312 |

FOREIGN PATENT DOCUMENTS

| | | |
|---|---|---|
| 0037175 | 3/1981 | European Pat. Off. . |
| 0078434 | 3/1981 | European Pat. Off. . |
| 0087864 | 1/1982 | European Pat. Off. . |
| 0071357 | 12/1982 | European Pat. Off. . |
| 1005007 | 6/1984 | Japan ................................... 514/558 |
| 989554 | 4/1965 | United Kingdom . |
| 1280244 | 7/1972 | United Kingdom . |
| 1440386 | 6/1976 | United Kingdom . |
| 1582992 | 7/1977 | United Kingdom . |
| 2012162 | 11/1977 | United Kingdom . |
| 1506563 | 4/1978 | United Kingdom . |
| 2090529 | 6/1980 | United Kingdom . |
| 2104907 | 7/1981 | United Kingdom . |
| 2134782 | 9/1982 | United Kingdom . |

*Primary Examiner*—Douglas W. Robinson
*Assistant Examiner*—Zohveh A. Fay
*Attorney, Agent, or Firm*—Wolder, Gross & Yavner

[57] ABSTRACT

The invention is concerned with the use of certain fatty acids and inhibitors of an enzyme in effecting modifications to the lipid structure of cell membranes. The invention also relates to the formulation of pharmaceutical compositions and medicaments and to such products per se; to the treatment of a variety of clinical and veterinary disorders associated with a lowering of the saturation index of cell membranes, including malignancies, viral disorders and AIDS; and to the use of the active materials of the invention in the relief of pain.

The active principals in the present invention are saturated fatty acids having from 12 to 28 carbon atoms in the alkyl chain, e.g. stearic acid, or pharmaceutically acceptable derivatives thereof; and inhibitors of the enzyme Δ-9 desaturase, e.g. sterculic acid and malvalic acid or pharmacologically active derivatives or analogues thereof.

7 Claims, 3 Drawing Sheets

Samples of cells analysed at various times post infection
with HSV1 (■), or HSV2 (●), or mock infection (▲).

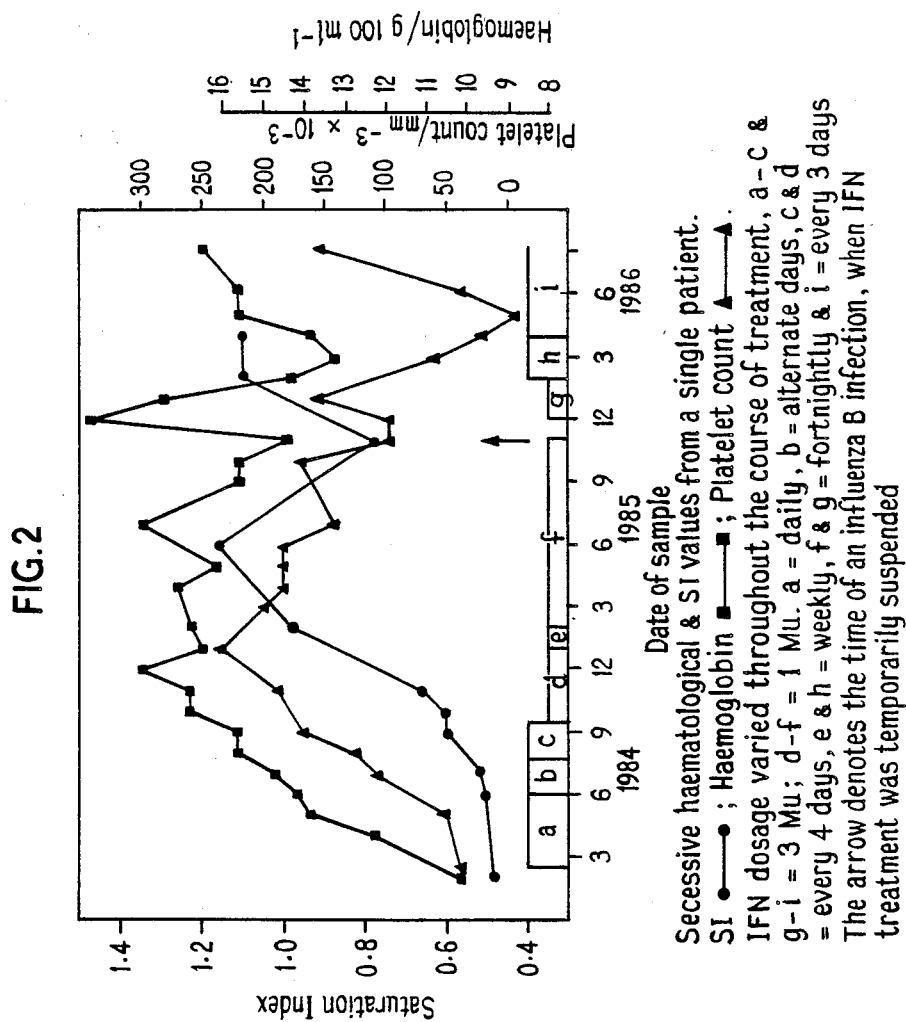

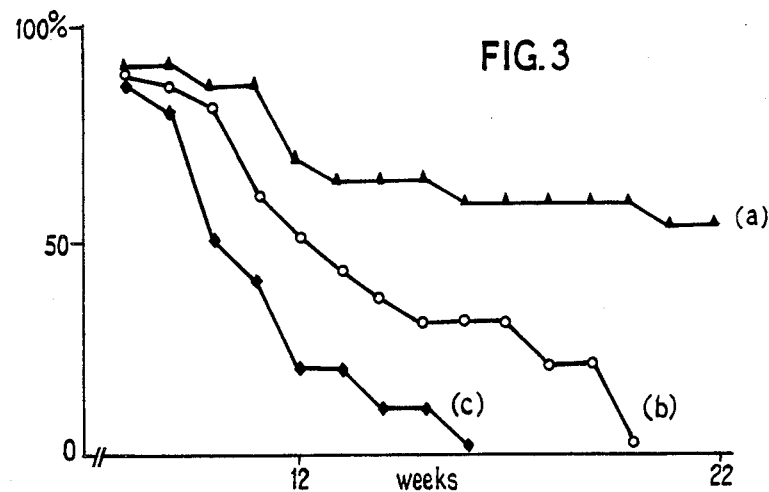
Percentage of tumour free animals in relation to treatment with (a) NMU; (b) NMU + interferon; (c) NMU + iodostearic acid
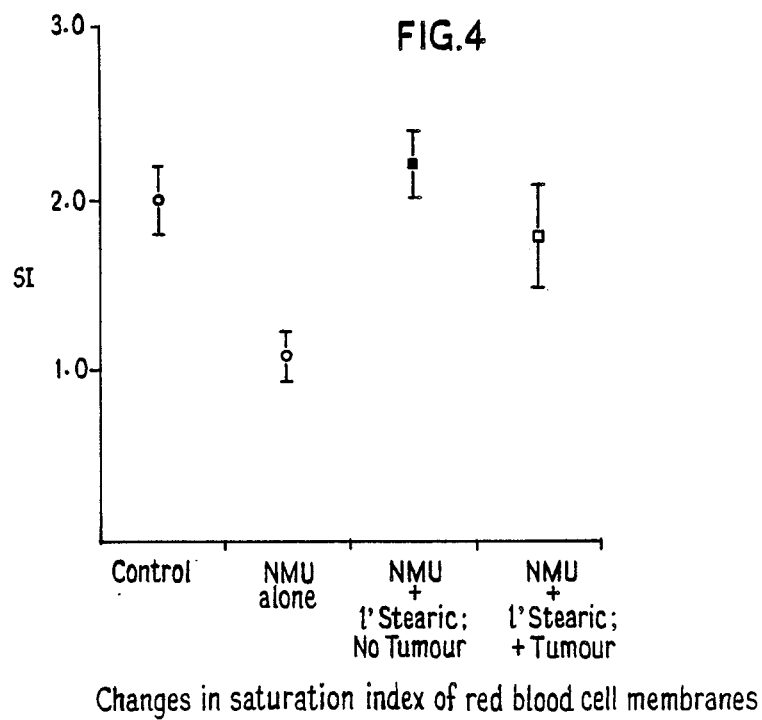
Changes in saturation index of red blood cell membranes

METHOD OF MODIFYING THE LIPID STRUCTURE AND FUNCTION OF CELL MEMBRANES AND PHARMACEUTICAL COMPOSITIONS FOR USE THEREIN

BACKGROUND OF THE INVENTION

This invention relates to methods for the modification of the lipid structure of cell membranes, to pharmaceutical compositions and methods for their administration and medicaments for use in the methods of the invention, to certain compounds and their derivatives for use in the treatment of disorders, and also relates inter alia to methods for the diagnosis and treatment of malignancy. The invention further relates to methods of treatment, both veterinary and clinical, based on the said compositions and medicaments.

There is a wide range of naturally occurring saturated and unsaturated fatty acids. These generally have an even number of carbon atoms in the chain. The C18 acids (for example stearic, oleic, linoleic and linolenic acids) are well known. Stearic acid is used as a lubricant in making compressed tablets and as an enteric coating for pills and tablets. The acid and its salts are well known as excipients in pharmaceutical formulations. It has also been used, when partly neutralised with alkalis or triethanolamine, as the basis of cosmetic preparations such as vanishing creams. It seems that the C12-C28 saturated fatty acids, e.g. stearic acid, were not hitherto known to have medicinal properties per se.

Both the physical stability of cell membranes and the regulation of a wide variety of metabolic processes, especially those involving membrane-associated enzymes, are dependent on the regulation of cell membrane lipid composition (Sandermann, H, Jr., (1978) Biochim. Biophys. Acta, 515, 209-237). This regulation provides for the homeostasis of membrane fluidity, predominantly through the balance between constituent saturated and unsaturated fatty acids (Doi, O; Doi, F; Schroeder, F; Alberts, A. W & Vagelos, P. R. (1978) Biochim. Biophys. Acta, 509, 239-250; and Quinn, P. J. (1983) Biochem. Soc. Trans. 11, 329-330). Analysis of cell membrane lipids shows that the most abundant species of fatty acids are the 18 carbon (C18) straight chain fatty acids of which the polyunsaturates (e.g. linoleic and linolenic) acids are derived from the diet. Further, the other main components of this family, octadecanoic acid (stearic acid) and cis-9-octadecenoic acid (oleic acid), differ widely in their melting points and so the relative proportions of these acids within the membrane is important in determining membrane fluidity. In normal resting cells, the degree of cell membrane fluidity appears to be associated with the rate of cell division, higher fluidity reflecting a higher rate of division, and vice versa. The enzyme Δ-9 desaturase is involved in the change from saturated to unsaturated fatty acids (Jeffcoat, R. and James, A. T. in New Comprehensive Biochemistry, publ. Elsevier, 1984, vol. 7, pp 85-112). Under normal circumstances the activity of this enzyme is regulated in accordance with requirements of the cell to produce more oleic acid in order to maintain a specific level of membrane fluidity. For convenience, the enzyme Δ-9 desaturase will be referred to as D9DS in the description which follows.

REVIEW OF THE PRIOR ART

The use of essential fatty acids in various clinical and veterinary treatments has been described in several published patent applications. For example, EP 0037175, EP 0071357, EP 0078434 and EP 0087864 (all in the name Efamol Ltd.) relate to the use of linolenic acid (LLA) and dihomo-gamma linolenic acid (GLLA). These fatty acids influence the prostaglandin cycle and are set forth as useful in the treatment of a number of didorders including multiple sclerosis, cancer, allergic and inflammatory disorders, disorders of lipid metabolism in which blood cholesterol levels are elevated, hypertension, mental illness, schizophrenia and depression. In treating all of these conditions, the active ingredients are said to be LLA and GLLA. Natural sources of GLLA are recommended for therapeutic use; these include oils derived from the seeds of Oenothera species (Evening Primrose) and *Borago officinalis* (Borage). These oils include fatty acids other than GLLA and LLA, the oil from *Oenothera biennis* typically containing about 1.5% stearic acid. The presence of stearic acid in these oils is merely incidental and is not taught as being of any beneficial effect.

GB No. 1506563 (John Williams) is also concerned with the therapeutic use of LLA and GLLA. These acids are said to be effective in treating neurological disorders and diseases and act as immuno-suppressive agents.

GB No. 2134782 (Sentrachem Limited) discloses the use of LLA and GLLA in the treatment of cancer. It is claimed that the defect in cancer cells is an inhibition of the enzyme Delta-6 desaturase which results in a block in the conversion of LLA to GLLA. The invention disclosed in this document involves the administration of GLLA, arachidonic acid, eicosapentaenoic acid or their derivatives. There is no disclosure of any therapeutic effect associated with stearic acid or its saturated homologues.

U.S. Pat. No. 4097602 (Melvin J. Silver et al.) discloses a method of inhibiting blood platelet aggregation by oral administration or parenteral administration of cis-8,11,14-eicosatrienoic acid which is said to influence the prostaglandin cycle. This polyunsaturated active ingredient may be combined with conventional aompatible organic or inorganic pharmaceutical carriers, including magnesium stearate. There is no teaching that magnesium stearate or stearic acid has any therapeutic effect per se. GB No. 1440386 (Geraldine Hudson Thiele) discloses a process of accelerating the healing of a mosaic bone fracture by the use (as scleroting agents) of a variety of fatty acids. All saturated fatty acids, regardless of the chain length (and including formic acid) are claimed to be of use. Stearic acid is mentioned, in a long list of acids, but there is no example indicating use of this acid or of any of its derivatives. The only fatty acid whose use in the process is exemplified is oleic acid.

GB No. 1280244 (Parke Davis & Co.) discloses the use of alkanedioic acids and their salts and alcohol esters in compositions for reducing the level of triglycerides in serum. The disclosed active ingredients may be admixed with conventional pharmaceutical carriers, of which stearic acid and magnesium stearate are mentioned amongst others. There is no teaching that stearic acid or its derivatives have any therapeutic effects per se.

GB No. 2104907 (Kureha Kagaka Kogyo KK) discloses the use of cyclodextrin as a stabilising reagent for eicosapentaenoic acid and docosahexaenoic acid, their salts and esters. The resulting inclusion compounds are said to reduce cholesterol levels in human serum.

GB No. 2090529 (Nippon Oil and Fats Co. Ltd.) discloses a thrombosis-preventing curative agent containing docosahexanoic acid or a derivative thereof. The active ingredient influences the prostaglandin cycle and antagonizes the action of arachidonic acid. Stearic acid is mentioned as one of many conventional excipients which may be incorporated with the active ingredient; there is no disclosure of stearic acid having any therapeutic properties per se.

GB No. 2012162 (Duncan Lee McCollester) discloses an injectable composition containing a source of manganous ions for use in the immunotherapy of neoplastic disease. One suitable source of the manganous ion is said to be manganous stearate. There is no teaching that the stearate moiety or its parent acid has any therapeutic properties per se. The manganous ion is said to stimulate the immune antigens and the nucleotide cyclase enzymes.

GB No. 1582992 (Proctor & Gamble) discloses the use of C4—C12 carboxylic acid derivatives in a water soluble solution for intravenous administration in order to inhibit the growth of microbes. There is no disclosure of the bacteriostatic and fungostatic properties of the active compounds.

BRIEF DESCRIPTION OF THE DRAWINGS

In the description which follows, reference will be made to the accompanying drawings, of which:

FIG. 2 illustrates values of the saturation index in a human patient undergoing treatment with interferon for the condition hairy cell leukaemia;

FIG. 3 illustrates the percentage of tumour free animals in an experiment involving the inoculation of rats with a carcinogen (described in detail in Example 3 hereinafter); and FIG. 4 illustrates the values of the saturation index measured during the experiment to which FIG. 3 relates.

Figure 1:
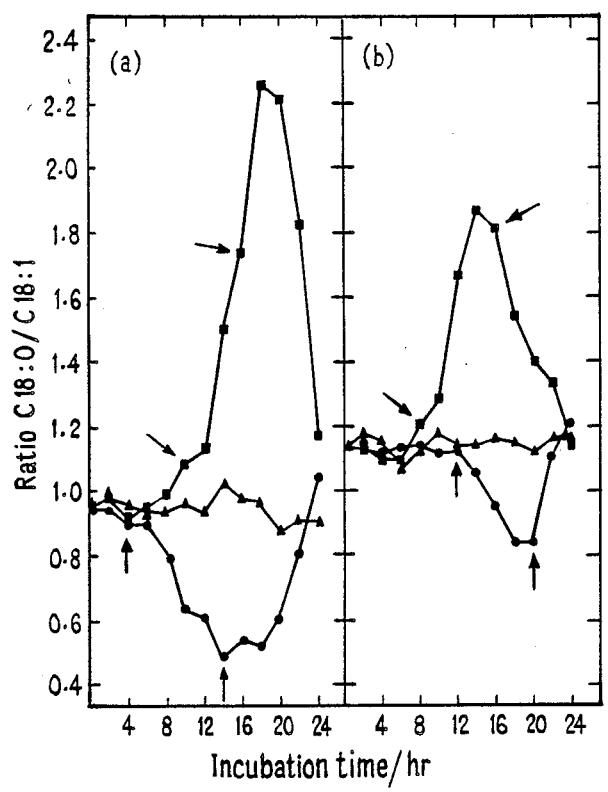
FIG. 1 illustrates changes in saturation index of cells after infection with oncogenic viruses.

Total lipid extracts of erythrocyte cell membranes from patients with documented malignancies, various acute and chronic diseases and healthy subjects have been analysed (British Medical Journal, 20 July 1985, 291, 163–165). The results were expressed as ratios of stearic to oleic acid, reflecting the degree of desaturation of stearic acid in the cell membranes. This ratio of saturated C18 fatty acid to monounsaturated C18 fatty acid, when determined by the gas-liquid chromatographic techniques described in the above-mentioned British Medical Journal article from total lipids extracted according to the method of Folch, J. et al, subsequently derivatised according to the method described by Blenkharn. J. I. & Apostolov, K. (Biochim, Biophys. Acta (1980), 597, 258–363), is referred to herein as the "saturation index". The mean index for healthy subjects and controls without cancer were 1.5 (SD±0.27) and 1.45 (SD±0.28), respectively, whereas the index for patients with malignancies were consistently lower than 1.0 with a mean value of 0.69 (SD±0.15) (p less than 0.001).

Cells transformed (immortalized) by oncogenic viruses have been shown to have a saturation index rather lower than normal control cells (Yau, T. M. & Weber, M. J. (1972) Biochem. Biophys. Res. Commun., 49, 114–119). FIG. 1 of the accompanying drawings illustrates the kinetic changes in the saturation index from total host cell membranes following infection with Herpes simplex virus (HSV1 and HSV2) of (a) baby hamster kidney cells and (b) human embryonic lung cells.

Also malignant tissue (cancer cells) obtained from patients during surgery show a lower saturation index than non-malignant tissue taken from the same organ in the same patient (Wood, C. B., Habib, N. A., Apostolov, K., Thompson, A., Barker, W., Hershman, M., and Blumgart, L. H., Europ. J. Surg. Oncol., 1985 II, 347–348).

White blood cells obtained from patients with leukaemia also show a lower saturation index than white blood cells of patients without leukaemia (Apostolov, K; Barker, W, Catovsky, D; Goldman, J. & Matutes, E. (1985) Blut, 50, 349–354), as indicated by the data in Table 1 below:

TABLE 1

| Sample type | Saturation index of blood cells from freshly collected specimens of normal blood | | | |
|---|---|---|---|---|
| | No. specimens | Mean | Range | s.d. |
| RBC | 16 | 1.534 | 0.189 | 0.064 |
| Granulocytes | 14 | 1.281 | 0.421 | 0.030 |
| Lymphocytes | 6 | 1.282 | 0.176 | 0.053 |
| WBC buffy coat | 16 | 1.322 | 0.195 | 0.047 |

Saturation index of WBC collected from patients with chronic granulocytic leukaemia (CGL). Index mean=0.506 s.d.=0.085. Cells were harvested using a cell separator and consequently red blood cells were not available for analysis

| Patient | WBC index | Patient | WBC index | Patient | WB index |
|---|---|---|---|---|---|
| AA | 0.485 | ED | 0.533 | SR | 0.547 |
| GB | 0.458 | CJ | 0.426 | MS | 0.488 |
| HB | 0.442 | EN | 0.640 | MS | 0.477 |
| SB | 0.483 | AP | 0.416 | PW | 0.561 |
| KC | 0.419 | AR | 0.707 | | |

Saturation index of RBC and WBC serially collected from patients with CGL. N/A=cases where too few RBC were available for analysis. Maximum variation in indices from a single patient: WBC=0.233: RBC=0.204.

| Patient | Day No. | WBC index | RBC index |
|---|---|---|---|
| KC | 1 | 0.476 | 0.511 |
| | 3 | 0.412 | 0.527 |
| | 4 | 0.376 | 0.649 |
| | 10 | 0.411 | 0.445 |
| ED | 1 | 0.429 | 0.462 |
| | 9 | 0.662 | N/A |
| | 19 | 0.507 | N/A |
| CJ | 1 | 0.395 | 0.492 |
| | 7 | 0.416 | 0.444 |
| | 13 | 0.469 | N/A |

Saturation index of RBC and WBC collected from patients with chronic lymphoid leukaemias. Specimens marked 'N/A'=too few RBC available for analysis. B-CLL=B-cell chronic lymphocytic leukaemia; BL=B-cell lymphoma; HCL=hairy cell leukaemia; T-PLL=T-cell prolymphocytic leukaemia; ATL-L=adult T-cell leukaemia lymphoma

| Patient | Leukaemia type | WBC index | RBC index |
| --- | --- | --- | --- |
| JC | B-CLL | 0.516 | N/A |
| WF | B-CLL | 0.888 | N/A |
| IG | B-CLL | 0.566 | 0.549 |
| ML | B-CLL | 0.718 | N/A |
| MO | B-CLL | 0.536 | N/A |
| SO | B-CLL | 0.761 | 0.934 |
| VP | B-CLL | 0.648 | 0.519 |
| CT | B-CLL | 0.626 | N/A |
| ET | B-CLL | 1.569 | N/A |
| AB | BL | 0.719 | 0.821 |
| HG | BL | 0.553 | N/A |
| GG | HCL | 0.675 | 0.504 |
| KO | HCL | 0.497 | 0.633 |
| GB | T-PLL | 0.611 | 1.209 |
| FF | T-PLL | 1.071 | 0.462 |
| RL | T-PLL | 0.684 | 0.537 |
| HS[a] | ATLL | 0.600 | 0.674 |

[a] = human T-cell leukaemia virus isolated from this patient. Mean WBC index = 0.720, s.d. = 0.261; mean RBC index = 0.684, s.d. = 0.238.

$a$ = human T-cell leukaemia virus isolated from this patient. Mean WBC index = 0.720, s.d. = 0.261; mean RBC index = 0.684, s.d. = 0.238.

The successful control of hairy cell leukaemia with interferon was shown to be accompanied by an increase in and normalisation of the saturation index. This is demonstrated in FIG. 2 of the accompanying drawings, which relates to a single patient who was given interferon (IFN) at different dosages during the course of treatment.

SUMMARY OF THE INVENTION

We have found that the application of stearic acid or iodostearic acid to malignant cells in vitro leads to over 50% inhibition of ras-oncogene product (molecular weight 21,000) determined by radioimmunoassay and flow cytometry, whereas application of oleic acid results in an increase in this product of around 400%. We therefore believe that the fluidity of the cell membrane can dictate oncogene expression within the cell.

According to one aspect the present invention provides a method of treating a clinical or veterinary disorder characterised by a lowering of the saturation index (as hereinbefore defined) compared to the norm, which method comprises administering to an affected human or non-human animal a therapeutically effective amount of a saturated fatty acid having from 12 to 28 carbon atoms in the alkyl chain, e.g. stearic acid, or a pharmaceutically acceptable derivative thereof.

According to another aspect the present invention provides a method of treating a clinical or veterinary disorder characterised by a lowering of the saturation index (as hereinbefore defined) compared to the norm, which method comprises administering to an affected human or non-human animal a therapeutically effective amount of an inhibitor of the enzyme Δ-9 desaturase, e.g. sterculic acid or malvalic acid or a pharmacologically acceptable derivative or analogue thereof.

According to a third aspect the present invention provides, for use in modifying the lipid structure of cell membranes, a saturated fatty acid having from 12 to 28 carbon atoms in the alkyl chain, e.g. stearic acid, or a pharmaceutically acceptable derivative thereof, prepared for parenteral, rectal or dermal administration. Pharmaceutically acceptable derivatives include salts, methylated derivatives, and esters such as sodium stearate, 9-methyl stearic acid, 10-methyl stearic acid and ethyl stearate. The heavy metal salts are not pharmaceutically acceptable because of the properties of the heavy metal cations and do not form any part of this invention. The mono-halogenated and di-halogenated derivatives (i.e. those compounds in which one or two of the hydrogen atoms in the alkyl chain is or are replaced by a halogen) are also pharmaceutically acceptable and may be beneficial in that the heavier substituted radical seems to increase the retention time in vivo. Parenteral, rectal or dermal administration is preferred because oral ingestion of these fatty acids leads to their degradation through the action of the digestive system and the liver. Dermal application can be effected as a cream or balm and may be applied to any part of the body, whether or not at a site of disease.

It has also now been found that the oral, topical or parenteral administration of inhibitors of the enzyme D9DS has a pronounced effect in raising the saturation index of cells in vivo. Accordingly, in another aspect, the invention provides, for use in modifying the lipid structure of cell membranes, an inhibitor of the enzyme D9DS (e.g. sterculic acid or a pharmacologically acceptable derivative or analogue thereof) prepared for parenteral, oral, rectal or dermal administration.

The seeds or nuts of the tropical tree *Sterculia foetida* contain an oil which contains a mono-unsaturated fatty acid, namely sterculic acid. This acid contains a cyclopropene ring ($C_3H_2$) and has the formula:

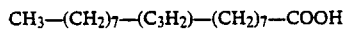
$$CH_3-(CH_2)_7-(C_3H_2)-(CH_2)_7-COOH$$

and is an inhibitor of the enzyme D9DS. Another inhibitor of this enzyme is malvalic acid, which also contains a cyclopropene ring ($C_3H_2$) and has the formula:

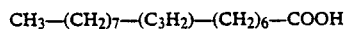
$$CH_3-(CH_2)_7-(C_3H_2)-(CH_2)_6-COOH$$

It is possible that other cyclopropenoid fatty acids, whether naturally occurring or synthetic, may have a similar inhibiting effect on the action of D9DS. Malvalic and sterculic acids may be extracted from other plants of the family Sterculiaceae, which belong to the order Malvales and occur principally in the tropics. Malvalic acid may, for example, be extracted from the seed oil of *Pterospermum acerifolium* (Canadian Journal of Biochemistry, 48, 1970, 759–762). The administration of sterculic acid in vitro to hepatoma cell lines has been observed to cause an increase in their saturation index with subsequent growth inhibition (Zoeller, M. A., and Wood, R., Lipids, 19, 7, 1984, 529–538).

The invention also provides, for use in the treatment of diseases characterised by a lowered saturation index (as hereinbefore defined), e.g. a saturation index of less than 1, (i) a saturated fatty acid having from 12 to 28 carbon atoms in the alkyl chain, e.g. stearic acid, or a pharmaceutically acceptable derivative thereof; or (ii) an inhibitor of D9DS, e.g. sterculic acid or a pharmacologically acceptable derivative or analogue thereof.

The invention also provides a medicament or pharmaceutical composition containing, as active ingredient, a saturated fatty acid having from 12 to 28 carbon atoms in the alkyl chain, e.g. stearic acid, or a pharmaceutically acceptable derivative thereof.

The invention also provides a medicament or pharmaceutical composition containing as active ingredient an inhibitor of the enzyme D9DS, e.g. sterculic acid and/or malvalic acid, or a pharmacologically active derivative or analogue thereof. Medicaments and pharmaceutical compositions which contain both (1) a saturated fatty acid having from 12 to 28 carbon atoms in the alkyl chain, e.g. stearic acid, or a pharmaceutically acceptable derivative thereof (e.g. iodostearic acid) and (2) an inhibitor of the enzyme D9DS, e.g. sterculic acid and/or malvalic acid, or a pharmacologically active derivative or analogue thereof also form part of this invention; such compositions are preferably prepared in a form suitable for oral administation.

The invention also provides, for use in the treatment of viral infections characterised by a lowering of the saturation index relative to the norm, a saturated fatty acid having from 12 to 28 carbon atoms in the alkyl chain, or a pharmaceutically acceptable derivative thereof, or an inhibitor of the enzyme D9DS (e.g. sterculic acid or a pharmaceutically active derivative thereof).

The invention further provides (i) the use of stearic acid or a pharmaceutically acceptable derivative thereof in the manufacture of a medicament or pharmaceutical composition for the treatment of benign and malignant neoplasms; (ii) use of an inhibitor of the enzyme D9DS in the manufacture of a medicament or pharmaceutical composition for the treatment of benign and malignant neoplasms; and (iii) use of sterculic acid or a pharmacologically active derivative or analogue thereof in the manufacture of a pharmaceutical composition for the treatment of benign and malignant neoplasms.

The invention further provides (i) use of saturated fatty acids having from 12 to 28 carbon atoms in the alkyl chain, or a pharmaceutically acceptable derivative thereof, in the manufacture of a medicament or pharmaceutical composition for the treatment of viral infections; (ii) use of an inhibitor of the enzyme D9DS in the manufacture of a medicament or pharmaceutical composition for the treatment of viral infections; and (iii) use of sterculic acid or a pharmacologically active derivative or analogue thereof in the manufacture of a pharmaceutical composition for the treatment of viral infections.

The invention further provides (i) use of saturated fatty acids having from 12 to 28 carbon atoms in the alkyl chain, or a pharmaceutically acceptable derivative thereof, in the manufacture of a medicament or pharmaceutical composition for the treatment of AIDS; (ii) use of an inhibitor of the enzyme D9DS in the manufacture of a medicament or pharmaceutical composition for the treatment of AIDS; and (iii) use of sterculic acid or a pharmacologically active derivative or analogue thereof in the manufacture of a pharmaceutical composition for the treatment of AIDS. The fatty acid in this embodiment may be used as a halogenated derivative, e.g. an iodinated derivative, or as a methylated derivative.

The medicaments and pharmaceutical compositions of this invention which incorporate C12-C28 saturated fatty acids are preferably prepared for parenteral administration. The medicaments and pharmaceutical compositions of this invention which incorporate an inhibitor of the enzyme D9DS may be prepared for topical or parenteral administration, although it will in many cases be more convenient for them to be prepared for oral administration. Where the medicaments and pharmaceutical compositions are prepared for oral, parenteral or rectal administration, they are conveniently provided in unit dosage form, e.g. as a unit dosage tablet, pill, capsule, lozenge, dragee, powder, suspension, ampoule or suppository.

The medicaments and pharmaceutical compositions of this invention may contain pharmaceutically acceptable diluents, excipients, solvents, emulsifiers and/or other conventional additives or ingredients which do not inhibit the action of the active ingredient. They may include a solvent or dispersant for the fatty acid if such acid is present.

Halogenated stearic acids may conveniently be prepared by olefinic addition of a hydrohalic acid, e.g. hydrogen iodide or hydrogen bromide, to oleic acid or by iodination using iodine in acetic acid, or with Lugol's solution and hydrogen peroxide.

Further aspects of the invention provide (i) an analgesic composition which comprises, as its active ingredient, a saturated fatty acid having from 12 to 28 carbon atoms in the alkyl chain, e.g. stearic acid, or a pharmaceutically acceptable derivative thereof; and, for use in the relief of pain associated with malignant disease, a composition comprising a saturated fatty acid having from 12 to 28 carbon atoms in the alkyl chain, e.g. stearic acid, or a pharmaceutically acceptable derivative thereof.

DETAILED DESCRIPTION OF THE INVENTION

The use of C18 fatty acids in preventing cell division of malignant cells and in preventing or reducing the replication of viruses in accordance with this invention has been investigated and will be described in the following Examples.

EXAMPLE 1

N-nitrosomethylurea (NMU) is a known carcinogen which rapidly induces mammary carcinoma in rats and does not require metabolic activation. NMU was administered intravenously to thirty female Sprague-Dawley rats weighing approximately 200 g. It has been well established that with this animal model breast cancers will develop in the majority by 12 weeks from the commencement of the giving of the carcinogen (Gullino, P. M., Pettigrew, H. M., and Grantham, E. H., I. National Cancer Inst. 1975, 54, 401–409). The rats were divided into two groups, with those of the first group (twenty rats) receiving NMU alone, and those of the second group (ten rats) receiving NMU plus stearic acid. NMU in 3% acetic acid was dissolved in distilled water (20 mg/ml) and was given in three intravenous injections of 5 mg/100 g body weight at weeks 1, 4 and 8. 10 mg stearic acid from Sigma Chemicals, U.K., was dissolved in 0.5 ml liquid paraffin and was injected at weekly intervals subcutaneously in the flank, starting from the second week. The onset of tumours was monitored by daily inspection and by palpation of the mammary regions twice weekly. At week 22, all surviving animals were sacrificed, and autopsies were performed. The tumours located thereby were dissected and examined histologically. In the control animals who were given carcinogen alone 19 out of the 20 animals had developed breast cancers by week 16 of the experiment, with a mean latent period of 72 days. These 19 rats had a total of 51 tumours, giving a mean value of 2.68 tumours/rat, the range being from 1 to 5. The range of tumour weight/rat was 5 g to 47.8 g with a mean value of 23.6 g per rat (excluding the tumour free animal). By comparison, of the animals given carcinogen plus saturated fatty acid (stearic acid) five of the original ten had developed mammary tumours by week 16 of the experiment, with a mean latent period of 74 days. These five rats had seven tumours in all, with a mean of 1.4 tumours per rat (p less than 0.001 compared to the control group). The range of tumour weight/rat was 4.2 g to 21.2 g, with an average of 16.4 g/rat (p less than 0.01 compared to the control group). By week 22, all 19 of the rats with tumours from the control group had died; in contrast, only 2 of the ten rats in the second group (receiving NMU and stearic acid) had died by week 22. Of the remaining 8 live rats from this group which were killed at week 22, only three had tumours, the other five being tumour-free. Histological examination of all of the tumours from both groups showed that they were adenocarcinomas.

We have also found that stearic acid inhibits the development of tumours in animals which have been implanted with malignant cells.

In vitro studies have been conducted using a clonogenic assay utilising three cancer cell lines from bladder, testis and hepatoma (liver cancer), incubating the cells for two weeks with saturated fatty acids. The control cells were incubated without any addition. The control cells grew during this time period and formed multiple colonies, as was expected. However the group that was treated with stearic acid failed to divide. The degree of inhibition of cell division was related to the dose of stearic acid. At a dose of 6 g/ml there was complete inhibition of cell division.

EXAMPLE 2

An investigation similar to that described in Example 1 was performed using iodostearic acid in place of stearic acid, since the iodo-derivative is more readily soluble in lipid solvent than the parent acid. Oleic acid was commercially purchased (Sigma Chemicals, UK) and iodinated by passing dry hydrogen iodide gas in nitrogen through oleic acid at 20° C. Excess iodine was removed at the end of the reaction by the addition of an excess of sodium thiosulphate. The product of these reactions was a mixture of 9 iodo-octadecanoic, 10 iodo-octadecanoic and 9,10 di-iodo-octadecanoic acids. These can be collectively referred to as iodinated stearic acid or iodostearic acid.

Sixty-nine female Sprague Dawley rats weighing approximately 200 g each were divided into four groups. The first group (10 animals) were injected with normal saline only and served as a control group. The second group (15 animals) was injected with NMU alone. The third group (21 animals) received NMU and alpha$_2$ interferon (Schering). The fourth group (23 animals) received NMU plus iodostearic acid dissolved in liquid paraffin. NMU in 3 per cent acetic acid was dissolved in distilled water (20 mg/ml) and given to the rats of all three groups in two intravenous injections of 7 mg/100 g body weight, the second injection following three weeks after the first. Alpha$_2$ interferon was administered intramuscularly to the rats in the second group in a dose of 80,000 iu/kg twice each week throughout the experiment. Iodostearic acid was given subcutaneously to the rats in the third group in a dose of 5 mg dissolved in liquid paraffin twice a week throughout the experiment starting from the fifth week.

Tumour onset was monitored as described in Example 1. Throughout the experiment only rats that had ulcerated tumours or developed cachexia and marked weakness were sacrificed.

When the rats were killed, blood was withdrawn via cardiac puncture and collected in EDTA bottles. Blood was withdrawn from living rats (without tumour) via the tail vein. The aim of this investigation was two-fold: first, to study the possible reduction of stearic to oleic acid ratio in the erythrocytes of rats during chemical carcinogenesis; and second, to investigate whether iodostearic acid modified the saturation index in tumour-free animals.

Rat erythrocytes were separated by centrifugation. Total lipid extraction was carried out following the method of Folch, J. et al, subsequently derivatised according to the method described by Blenkharn. J. I. & Apostolov, K. (Biochim. Biophys. Acta (1980), 597, 258–363). The extracts were analysed blind using temperature-programmed (160° C. to 260° C. at 4° per minute) gas liquid chromatography (GLC) of the fatty acid methyl-esters utilising a 2.1 m$\times$2 mm internal diameter glass column packed with 3% SP-2310/2% SP-2300 on 100/120 mesh chromosorb W (Supelco Inc). Using this method it was possible to separate C16, C18, C20 and C22 fatty acids. The ratio of stearic:oleic fatty acids was taken from the GLC tracing and was expressed as the saturation index (SI). Comparison of indices was made using Student's unpaired 't' test.

FIG. 3 shows the results of this experiment. In the second group (NMU alone) one rat died following the first injection of carcinogen. On the remaining 14 animals, all developed tumours with a mean latent period of 74 days. These rats had 54 tumours between them, giving a mean of 3.8 tumours/rat (range 1–6). Tumour weight/rat ranged from 5 g to 53.5 g with a mean of 23.6 g tumour/rat.

Two rats in the third group (NMU plus interferon) died following carcinogen injection. All the remaining 19 rats developed tumour, with a mean latent period of 77 days. The rats with tumour had 63 tumours between them (range 1–6) with a mean of 3.3 tumours/rat. Tumour weight/rat ranged from 3.8 g to 34.5 g with a mean of 19 g/rat. None of these results were appreciably different from controls.

In the third group tested with NMU and iodostearic acid, four rats died following carcinogen injection. Of the remaining 19 rats, 8 developed tumour with a mean latent period of 76 days. The eight rats had a mean of 2.7 tumours/rat, with a range of 1–5. Four had extensive tumours (more than 4 cm in diameter), and two had tumours between 2–4 cm. The remaining two rats had massive tumours ($>4$ cm) which regressed subsequently to less than 2 cm on continued treatment with iodostearic acid. At week 22, eleven of the 19 rats treated with NMU plus iodostearic acid were still alive and without tumour.

All the tumours in each of the groups was examined histologically and found to be adenocarcinomas.

FIG. 4 shows the mean and standard deviation of the saturation index (SI) in each group of rats. The mean SI of the normal saline control group was 2.0$\pm$0.3. In the NMU alone group, the erythrocyte SI fell consistently in all rats ($p<0.001$) to a mean of 1.09$\pm$0.28. Similarly, the SI was significantly reduced in rats receiving interferon (mean$=1.1\pm0.16$). By contrast, those rats receiving iodostearic acid that were tumour-free had an SI of 2.12$\pm$9.42. Moreover, the tumour-bearing animals receiving iodostearic acid had an SI (mean 1.79$\pm$0.33) that was higher than the group with NMU alone ($p<0.002$), but lower than that of tumour-free animals.

EXAMPLE 3

Assessment of tumour cell inhibition by stearic acid was measured using both rat and human cell lines by clonogenic assay. Cells from rat mammary carcinoma (Sp 22), primary rat fibroblasts (from alveolar tissue) and four rat hepatoma cell lines (D23, D261, D262A and D262B) were studied.

The method used for rat cells was as follows: 200 cells were plated per dish in 1 ml 'Eagles' methionine enriched medium (MEM)+10% newborn calf serum (NBCS) in 30 mm culture dishes and incubated for four hours at 37° C. All became firmly adherent during this initial incubation. Stock solution of stearic acid at 10 mg/ml in ethanol was prepared and added to MEM+NBCS at the level of 1% ethanol/100 g/ml stearic acid. Dilutions containing 20 g/ml, 2 g/ml, 200 ng/ml and 2 ng/ml were prepared. 1 ml of each dilution was added to four dishes of cells, the final concentration being half the concentration of the material added. At the highest stearic acid concentration the ethanol concentration was 0.5%. To control dishes 1 ml of MEM+NBCS was added, or 1 ml of MEM+NBCS+1% ethanol. The dishes were incubated for 5 days. Medium was then removed, and the cell colonies were rinsed with 0.9% W/V NaCl solution and fixed for 15 minutes with methanol. Cell colonies were stained with 1% aqueous crystal violet and the dishes were allowed to dry. Colonies were counted under a stereoscopic microscope, and colony formation at each stearic acid concentration was expressed as a percentage of that in the medium control (100%).

The human tumour cell lines were investigated as follows: 500 exponentially-growing RT112 (transitional cell carcinoma of the bladder) cells or two hundred 833K (non-seminomatous testicular germ cell tumour) cells were plated in 5 cm dishes in RPMI1640 medium supplemented with 5% foetal calf serum and 2 mM 1-glutamine. After 48 hours culture this was replaced with fresh medium alone or medium containing stearic acid. The stearic acid was dissolved in ethanol and diluted in medium to give final concentrations of between 1-10 g/ml. Following a further 14 days incubation colonies were fixed, stained and counted. Colony-forming efficiency of the treated cells was expressed as a proportion of that in the controls. The experiments were repeated three times to permit statistical analysis.

Table 2 below demonstrates that stearic acid, at a dose of 10 g/ml, caused significant inhibition of colony formation in the four rat hepatoma cell lines. It failed to inhibit the mammary carcinoma (Sp22) or the primary fibroblast colony development. Table 3 below shows that stearic acid inhibited colony formation by the human 833K and RT112 cell lines, in a dose-related response.

TABLE 2

Tumour cell colony inhibition test by stearic acid using rat cell lines

| Target cells | Treatment | Mean no colonies ± SE | % plating efficiency | % colony formation relative to medium control | P value* |
|---|---|---|---|---|---|
| Sp22 Rat mammary carcinoma | medium control | 61.0 ± 6 | 30.5 | | |
| | 0.5% ethanol | 61.5 ± 4 | 30.7 | | |
| | stearic acid 1 ng/ml | 54.0 ± 10 | 27.0 | 83 | NS |
| | 10 ng/ml | 55.7 ± 3 | 27.8 | 91 | NS |
| | 100 ng/ml | 52.5 ± 6 | 26.2 | 86 | NS |
| | 1 µg/ml | 56.7 ± 3 | 28.3 | 93 | NS |
| | 10 µg/ml | 58.7 ± 1 | 29.3 | 96 | NS |
| | 50 µg/ml | 51.2 ± 6 | 25.6 | 84 | NS |
| Primary rat fibroblasts (from alveolar tissue) | medium control | 55.0 ± 4.6 | 27.9 | | |
| | 0.5% ethanol | 44.7 ± 1.8 | 22.3 | | |
| | stearic acid 1 ng/ml | 49.5 ± 9.5 | 24.7 | 90 | NS |
| | 10 ng/ml | 59.7 ± 3.1 | 29.8 | 108.5 | NS |
| | 100 ng/ml | 47.2 ± 9.4 | 23.6 | 85.8 | NS |
| | 1 µg/ml | 48.5 ± 9.2 | 24.2 | 88.2 | NS |
| | 10 µg/ml | 52.0 ± 7.7 | 26.0 | 96.5 | NS |
| | 50 µg/ml | 47.5 ± 6.0 | 23.0 | 86.4 | NS |
| D23 Rat hepatoma | medium control | 41.8 ± 3.5 | 20.9 | | |
| | 0.5% ethanol | 46.5 ± 1.1 | 23.2 | | |
| | stearic acid 10 ng/ml | 42.3 ± 1.6 | 21.1 | 101.2 | NS |
| | 100 ng/ml | 37.0 ± 1.5 | 17.5 | 88.5 | NS |
| | 1 µg/ml | 28.0 ± 1.5 | 14.0 | 67.0 | <0.02 |
| | 10 µg/ml | 28.0 ± 2.9 | 14.0 | 67.0 | <0.02 |
| | 50 µg/ml | 10.0 ± 2.6 | 5.0 | 23.0 | <0.03 |
| D261 Rat hepatoma | medium control | 33.0 ± 5.1 | 16.5 | | |
| | 0.5% ethanol | 30.0 ± 2.4 | 15.0 | | |
| | stearic acid 1 µg/ml | 21.0 ± 3.0 | 10.6 | 64.5 | <0.05 |
| | 10 µg/ml | 18.0 ± 1.5 | 9.0 | 54.5 | <0.01 |
| | 50 µg/ml | 6.0 ± 3.0 | 3.0 | 18.1 | <0.001 |
| D262A Rat hepatoma | medium control | 245.0 ± 11.9 | 122.5 | | |
| | 0.5% ethanol | 236.7 ± 8.2 | 118.3 | | |
| | stearic acid 10 ng/ml | 216.0 ± 8.8 | 108.0 | 88.0 | NS |
| | 100 ng/ml | 247.8 ± 8.3 | 123.9 | 101.1 | NS |
| | 1 µg/ml | 203.8 ± 18.1 | 101.9 | 83.2 | NS |
| | 10 µg/ml | 190.3 ± 13.6 | 95.2 | 74.7 | <0.05 |
| | 50 µg/ml | 79.3 ± 7.1 | 39.6 | 32.4 | <0.002 |
| D262B Rat hepatoma | medium control | 37.0 ± 4.0 | 18.5 | | |
| | 0.5% ethanol | 34.0 ± 9.5 | 17.0 | | |
| | stearic acid 10 ng/ml | 40.3 ± 1.8 | 20.1 | 108.9 | NS |
| | 100 ng/ml | 41.0 ± 1.8 | 20.5 | 110.8 | NS |
| | 1 µg/ml | 31.0 ± 5.8 | 15.5 | 83.8 | NS |
| | 10 µg/ml | 25.0 ± 2.8 | 12.5 | 67.6 | <0.05 |

TABLE 2-continued

Tumour cell colony inhibition test by stearic acid using rat cell lines

| Target cells | Treatment | Mean no colonies ± SE | % plating efficiency | % colony formation relative to medium control | P value* |
|---|---|---|---|---|---|
| | 50 μg/ml | 18.0 ± 4.5 | 9.0 | 48.6 | <0.02 |

*Significance of difference between treated dishes and medium controls (student t-test) NS Not Significant

TABLE 3

Tumour cell colony inhibition test by stearic acid using human carcinoma cell lines

| Stearic acid Concentration (μg/ml) | Colony-forming ability RT112 | (± standard error 833K |
|---|---|---|
| 1 | 92.0% ± 13.5 | 81.5% ± 3.0 |
| 2 | 86.0% ± 10.5 | 70.4% ± 12.0 |
| 4 | 45.0% ± 6.6 | 27.5% ± 2.0 |
| 6 | 4.6% ± 0.7 | 0.9% ± 0.5 |
| 8 | 0.3% ± 0.3 | 0% |
| 10 | 0% | 0% |

EXAMPLE 4

Stearic and iodinated stearic acids were assayed for their inhibitory effects on the replication of type 2 herpes simplex virus (HSV) in sub-confluent monolayer cultures of human embryonic lung fibroblasts. The stearic acids used were commercial preparations from Sigma Chemical Company; the iodinated stearic acid was prepared by iodination of oleic acid. This was accomplished by reacting hydriodic acid with oleic acid in acetic acid at 20° C. Excess iodine was removed at the end of the reaction by the addition of an excess of sodium thiosulphate, and the product fatty acid was extracted into hexane. Acetic acid contamination of the iodinated stearic acid was removed by chromatographic separation on silicic acid. The product of these reactions was a mixture of 9-iodo-octadecanoic, 10-iodo-octadecanoic and 9,10-di-iodo-octadecanoic acids; these are collectively referred to herein as iodinated stearic acid for convenience.

Bovine serum albumin conjugates of the fatty acids (prepared according to the method of A. A. Spector and J. C. Hoak, J. Anal. Biochem. 1969, 32, 297–302) were added to the cell culture medium at various concentrations in the range 25–100 micromolar final concentration and at various times before and after (from 0 to 12 hours) infection with partially purified clinical isolates of HSV type 2, at a multiplicity of infection of 0.1 plaque forming units/cell.

28 hours after infection the titre of infectious virus in the culture supernatants was determined by standard infectious centre techniques on fresh human embryonic lung fibroblasts.

Stearic acid added in an amount up to a concentration of 75 micromolar in the culture medium showed maximum anti-viral activity against type 2 HSV (48% reduction in virus yield), when cells were treated for 3–4 hours before infection. Above this concentration, there was no further significant anti-viral activity. At a concentration of 100 micromolar, stearic acid inhibits cell division, as measured by cell counting. This is illustrated in Table 4 below:

TABLE 4

Effect of stearic acid on HSV2 replication

| Time relative to infection/ hours | Fatty acid concentration/μM | | | | | | | | | |
|---|---|---|---|---|---|---|---|---|---|---|
| | 0 | | 25 | | 50 | | 75 | | 100 (+) | |
| | (a) | (b) | (a) | (b) | (a) | (b) | (a) | (b) | (a) | (b) |
| −12 | | | 4.63 | 0 | 4.75 | 0 | 3.96 | 8 | 4.72 | 0 |
| −8 | | | 3.88 | 10 | 4.62 | 0 | 4.18 | 3 | 4.33 | 0 |
| −4 | | | 4.25 | 2 | 3.98 | 8 | 2.25 | 48 | 3.45 | 20 |
| −3 | | | 4.15 | 4 | 3.15 | 27 | 2.31 | 47 | 2.80 | 35 |
| −2 | | | 3.72 | 14 | 3.02 | 30 | 2.69 | 38 | 2.77 | 36 |
| −1 | | | 4.06 | 6 | 3.14 | 27 | 2.54 | 41 | 3.04 | 30 |
| 0 | 4.32 (*) | 0 | 4.43 | 0 | 4.00 | 7 | 3.55 | 18 | 3.85 | 11 |
| 1 | | | 4.11 | 5 | 3.96 | 8 | 4.44 | 0 | 3.71 | 14 |
| 2 | | | 4.31 | 0 | 4.45 | 0 | 3.92 | 9 | 3.96 | 8 |
| 3 | | | 3.89 | 10 | 3.88 | 10 | 4.53 | 0 | 3.83 | 11 |
| 4 | | | 4.26 | 1 | 4.36 | 0 | 4.21 | 3 | 4.52 | 0 |
| 8 | | | 4.41 | 0 | 4.09 | 5 | 3.87 | 10 | 4.03 | 7 |
| 12 | | | 4.21 | 3 | 3.92 | 9 | 4.11 | 5 | 4.28 | 1 |

(a) = virus yield × $10^{-3}$/pfu ml$^{-1}$
(b) = % reduction in virus yield compared with control cultures (*)
(+) = some inhibition of cell growth at this concentration of fatty acid supplementation Iodinated stearic acid exhibited similar activity to the non-iodinated acid, having a maximum effect when cells were pre-treated for 3–4 hours before infection, but it proved to be more toxic to the cells than stearic acid, having an optimum effective concentration (50% inhibition) at 40 micromolar. The results are shown in Table 5 below:

TABLE 5

Effect of iodostearic acid on HSV2 replication

| Time relative to infection/ hours | Fatty acid concentration/μM | | | | | | | |
|---|---|---|---|---|---|---|---|---|
| | 0 | | 20 | | 40 | | 60 (+) | |
| | (a) | (b) | (a) | (b) | (a) | (b) | (a) | (b) |
| −12 | | | 4.77 | 0 | 3.93 | 9 | 3.68 | 15 |
| −8 | | | 4.46 | 0 | 3.79 | 12 | 3.77 | 13 |
| −4 | | | 4.37 | 0 | 3.15 | 27 | 3.51 | 19 |
| −3 | | | 3.42 | 21 | 2.18 | 50 | 2.03 | 53 |
| −2 | | | 3.89 | 10 | 3.86 | 11 | 4.15 | 4 |
| −1 | | | 3.77 | 13 | 3.52 | 19 | 3.67 | 15 |
| 0 | 4.32 (*) | 0 | 4.05 | 6 | 3.88 | 10 | 2.66 | 38 |
| 1 | | | 4.53 | 0 | 4.03 | 7 | 2.31 | 47 |
| 2 | | | 4.26 | 1 | 4.23 | 2 | 2.82 | 35 |
| 3 | | | 4.62 | 0 | 3.92 | 9 | 4.22 | 2 |
| 4 | | | 4.48 | 0 | 4.51 | 0 | 3.74 | 13 |

TABLE 5-continued

| | Effect of iodostearic acid on HSV2 replication | | | | | | | |
|---|---|---|---|---|---|---|---|---|
| Time relative | Fatty acid concentration/μM | | | | | | | |
| to infection/ | 0 | | 20 | | 40 | | 60 (+) | |
| hours | (a) | (b) | (a) | (b) | (a) | (b) | (a) | (b) |
| 8 | | | 4.85 | 0 | 4.45 | 0 | 2.94 | 32 |
| 12 | | | 4.38 | 0 | 4.25 | 2 | 3.86 | 11 |

(a) = virus yield × $10^{-3}$/pfu ml$^{-1}$
(b) = % reduction in virus yield compared with control cultures (*)
(+) = some degree of cytotoxicity produced at this concentration of fatty acid supplementation

EXAMPLE 5

Observations have been made of the saturation index of erythrocytes and leucocytes in patients suffering from AIDS (acquired immunodefiency syndrome). The values obtained were consistently lower than in healthy controls. Typically the saturation index in erythrocytes from AIDS patients was about 0.2 and in leucocytes it was 0.1. These values were obtained using a modification of the extraction methods previously described which produces normal values (i.e. those in healthy subjects) typically of 0.9 for erythrocytes and 0.7 for leucocytes. Initial tests indicate that the administration of a medicament or pharmaceutical composition in accordance with this invention may raise and normalise the saturation index of the cells of AIDS patients. This may result in the course of the disease being retarded by inhibition of virus replication, and further may improve the condition of AIDS patients by reversing the systemic effects induced by the AIDS virus.

EXAMPLE 6

Twenty patients with advanced malignancies (gastrointestinal, breast, bone, renal and lung) for whom conventional therapy had failed were injected twice weekly with 2 g iodostearic acid intramuscularly in the buttock for three months. It was observed that this treatment caused no toxicity or side effects in any of the patients. Subjective improvement was observed in most patients in particular relief of pain, and, in the majority of these patients, objectively resulted in stabilising their condition. The patients were treated for a period of 13 weeks. During this period 8 of the 12 patients who were receiving no other medication experienced relief of pain. At the end of the period, two of the twenty patients displayed tumour regression, and in 14 the tumour had stabilised. The saturation index of the erythrocytes in sixteen of the twenty patients had risen by the end study. In eight of these patients, the saturation index prior to commencement of treatment was less than 0.5 and the rise in saturation index was only small despite stabilisation of their tumours. The other eight patients showed a significant increase in saturation index, as shown in Table 6 below:

TABLE 6

| Patient | SI before treatment | SI after treatment |
|---|---|---|
| 1 | 0.48 | 0.83 |
| 2 | 0.51 | 0.93 |
| 3 | 0.45 | 0.78 |
| 4 | 0.39 | 0.65 |
| 5 | 0.61 | 0.87 |
| 6 | 0.55 | 0.72 |
| 7 | 0.47 | 0.83 |
| 8 | 0.44 | 0.79 |

The invention can be used in diagnosis and treatment of malignant as well as non-malignant conditions. D9DS inhibitors other than those specifically recited herein may also be used.

It will be appreciated that the pharmaceutical compositions of the invention may be prepared by mixing together the active ingredient(s) together with a conventional vehicle or excipient or diluent where appropriate.

A suitable excipient for intramuscular administration is liquid paraffin. Conventional vehicles, excipients and diluents include gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; vegetable oils such as peanut oil, cotton-seed oil, sesame oil, olive oil, corn oil, and oil of theobroma; propylene glycol; glycerine, sorbitol; polyethylene glycol; water; agar; alginic acid; isotonic saline; and phosphate buffer solutions; as well as other compatible substances normally used in pharmaceutical formulations. The compositions of the invention intended for oral administration can also contain other components such as colouring agents, flavouring agents, and/or preservatives. These materials, if present, are usually used in relatively small amounts. The compositions can, if desired, also contain other therapeutic agents provided that these are compatible with the active ingredients in accordance with this invention.

For formation of tablets, use may be made of vehicles such as lactose, cane sugar, sodium chloride, glucose, urea, starch, calcium carbonate, kaolin, crystalline cellulose, and silicic acid; binders, such as water, ethanol, propanol, syrup, glucose, glycol, glycerin, starch solution, gelatin solution, carboxylmethyl cellulose, shellac, methyl cellulose, potassium phosphate and polyvinyl pyrrolidone; disintegrators, such as starch, sodium alginate, agar powder, laminaria powder, sodium hydrogencarbonate, calcium carbonate, sodium laurylsulfate, lactose and the like; disintegrate inhibitors, such as cane sugar, cacao butter and hydrogenated oils; adsorption accelerators, such as quaternary ammonium salts, and sodium laurylsulfate; humidifiers, such as glycerin and starch; adsorbents, such as starch, lactose, kaolin, bentonite and colloidal silicic acid; and lubricants, such as purified talc, boric acid powder and solid polyethylene glycol. For formation of pills, as carriers, use may be made of vehicles, such as glucose, lactose, starch, cacao fat, hardened vegetable oils, kaolin and talc; binders, such as Arabian rubber powder, tragacanth powder, gelatine and ethanol; and disintegrators, such as laminaria and agar. Tablets may be used by applying a conventional coating, for example sugar-coated tablets, gelatin-coated tablets, intestine soluble coated tablets, film-coated tablets or double layer tablets or multi-layer tablets. For formation of suppositories, as carriers, use may be made of polyethylene glycol, cacao fat, higher alcohols, esters of higher alcohols, gelatine and semi-synthesized glyceride. When injections are prepared, it is preferable that the solutions of suspensions are sterilized, and for preparation of solution, emulsion and suspension formulations, as diluents, use may be made of water, ethyl alcohol, propylene glycol, ethoxyisostearyl alcohol, polyoxyisostearyl alcohol, polyoxyethylene sorbit, sorbitan esters etc. In this case, an amount of salt, glucose or glycerin sufficient to prepare isotonic solutions may be contained in the formulations. For preparation of paste, cream, gel or suspension formulations, as diluents, use may be made of white vaseline paraffin, glycerin, cellulose derivatives, polyethylene glycol, silicone or bentonite.

In the present invention, pharmaceutically acceptable salts and esters include alkali metal, alkaline earth metal and other metal salts, such as the sodium, potassium, aluminium and calcium salts etc.; the ammonium salt, amine salts, e.g. norpholine, piperadine, trimethylamine, diethylamine salts, and lower alcohol esters, e.g. the methyl ester or ethyl ester.

In addition, the active component of the present invention may be given in the necessary amount to the patients in the form of a glyceride.

We claim:

1. A composition for the modification of the lipid structure of cell membranes and for elevation of the ratio of saturated to unsaturated lipids therein as indicated by the Saturation Index, said composition containing as an essential active ingredient, at least one compound selected from the group consisting of stearic and iodostearic acid in a form suitable for parenteral, rectal or subdermal administration.

2. The composition according to claim 1 wherein said essential active ingredient is stearic acid.

3. The composition according to claim 1 wherein said essential active ingredient is an iodostearic acid.

4. The method for raising the Saturation Index in patients having clinical conditions where the status of the lipid ratio in the cellular membranes shows reduced Saturation Index levels which method comprises the steps of administering to such patients by subdermal, rectal or parenteral routes, effective amounts of stearic or iodostearic acid.

5. The method of providing analgesia in those painful clinical conditions showing a reduced Saturation Index which comprises the steps of administering by parenteral, rectal or subdermal routes, an effective amount of stearic acid or an iodostearic acid to patients requiring analgesia for such conditions.

6. The method according to claim 5 where said conditions include benign and malignant growths, viral infections and the painful side-effects of AIDS.

7. The method according to claim 4 where said stearic acid or said iodostearic acid is administered in unit doses via a pharmaceutically acceptable vehicle.

* * * * *